United States Patent [19]
Klapper et al.

[11] Patent Number: 5,300,022
[45] Date of Patent: Apr. 5, 1994

[54] URINARY CATHETER AND BLADDER IRRIGATION SYSTEM

[76] Inventors: Martin Klapper, 333 Silver Lake Scotchtown Rd., Middletown, N.Y. 10940; Rudy Wunner, Foggintown Rd., Brewster, N.Y. 10509

[21] Appl. No.: 974,791

[22] Filed: Nov. 12, 1992

[51] Int. Cl.⁵ .................... A61M 1/00; A61M 3/02; A61M 31/00; A61M 37/00

[52] U.S. Cl. ..................... 604/35; 604/30; 604/39; 604/43; 604/45; 604/56; 604/82; 604/83; 604/96; 604/97; 604/98; 604/902; 604/264; 604/266

[58] Field of Search ............... 604/82, 83, 89, 96–102, 604/131, 149, 173, 264, 280, 30–35, 39–45, 56, 67, 246–247, 266–267, 902; 604/191–194

[56] References Cited

U.S. PATENT DOCUMENTS

| | | | |
|---|---|---|---|
| 2,139,653 | 12/1938 | Belfrage | 604/42 |
| 4,114,625 | 9/1978 | Onat | 604/96 |
| 4,299,226 | 11/1981 | Banka | 604/97 |
| 4,318,402 | 3/1982 | Vaillancourt | 604/280 |
| 4,487,600 | 12/1984 | Brownlie et al. | 604/35 |
| 4,493,694 | 1/1985 | Wuchinich | 604/35 |

Primary Examiner—Randall L. Green
Assistant Examiner—P. Zuttarelli
Attorney, Agent, or Firm—Sandra M. Kotin

[57] ABSTRACT

An improvement over the Foley catheter which provides, in addition to the main drainage lumen, a central smaller lumen for continuous delivery of a small quantity of sterile irrigating solution directly through the distal tip into the bladder. A larger portion of the irrigating solution is deflected by the cone shaped roof of the distal tip and turned backward past the drainage ports and into the drainage lumen. This backward flow of liquid causes a mild suction which assists the removal of clots and tissue debris from the bladder. The continuous flow of sterile solution also cleanses the drainage lumen and prevents the upward movement of bacteria common in most urinary catheters. A suction syringe can also be used in the usual manner in the event of a blockage. A second embodiment of the invention provides two protuberances across from the drainage ports within the distal tip to assist in breaking up clots as they enter the drainage lumen.

10 Claims, 3 Drawing Sheets

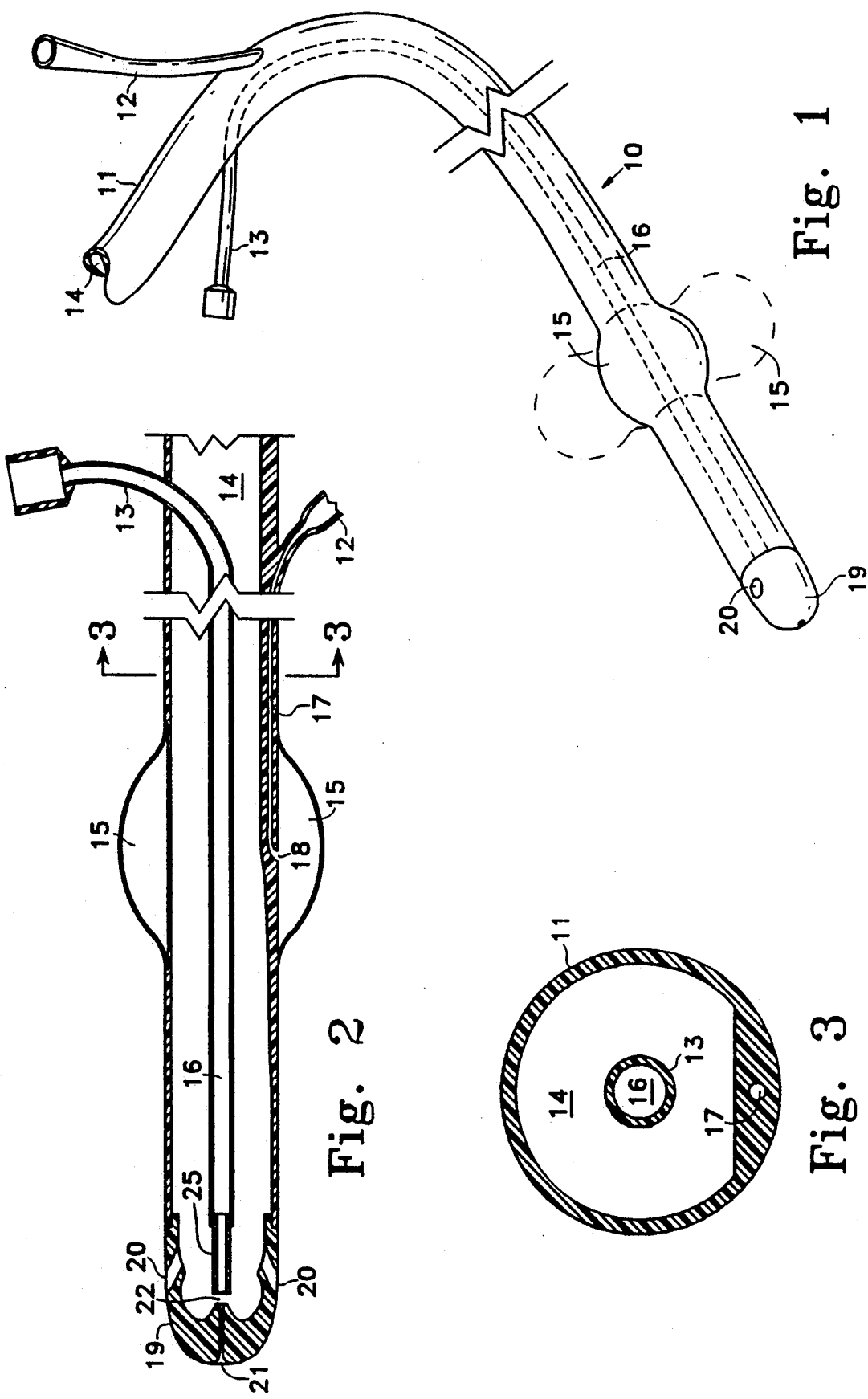

5,300,022

URINARY CATHETER AND BLADDER IRRIGATION SYSTEM

FIELD OF THE INVENTION

The instant invention relates to an indwelling urinary catheter which permits the continuous collection of urine and is capable of providing irrigation of the bladder, cleansing of the drainage lumen and mild suction means to break up and dislodge any clots and debris which may clog the drainage ports.

BACKGROUND OF THE INVENTION

Urinary catheters have been used for many years both for patients recovering from surgery and for those who are incontinent. In patients recovering from bladder and prostate surgery blood clots and clumps of tissue and debris often form which require frequent periodic irrigation of the bladder. This irrigation is performed through the catheter and can cause a great deal of pain and discomfort to the patient.

After a catheter has been in place for more than three of four days there is an almost certainty of bacterial infection of the urinary tract which may eventually spread to the kidneys if the catheter must remain in place for extended periods. The infection has been attributed to microorganisms moving up through the drainage tube and into the lumen of the catheter and finally to the bladder. Microorganisms may also become trapped in the urethra where they can reproduce.

Little has been done to improve the catheter since the development of the well-known Foley Catheter which provides an inflatable balloon near its distal end to retain the catheter in the bladder. Goldman fitted his catheter with a rigid section to prevent collapse of the lumen when pressure is exerted to inflate the balloon (U.S. Pat. No. 2,819,718).

Several catheters have been developed which permit cleansing of the main lumen to reduce the chance of having bacteria enter the bladder, but the cleansing solution is not permitted to enter the bladder and has nothing to do with bladder irrigation. Godfrey, in U.S. Pat. No. 4,227,533 teaches a flushable urinary catheter fitted with a valve such that a cleansing solution can be used to flush the catheter but the solution cannot pass the valve to enter the bladder. The catheter is cleansed up to the point of the valve. Kay also provides for a catheter which is fitted with a cleansing unit. The drainage ports of the catheter can be closed when the cleansing solution is introduced. Here too the lumen of the catheter can be cleansed without the solution entering the bladder (U.S. Pat. No. 4,723,946).

Christopher, in U.S. Pat. Nos. 4,571,241 and 4,710,169, describes a catheter with a collapsable wall portion which inflates with the flow of urine. The urethra is only extended as is that portion of the catheter when there is a urine flow, so that bacteria do not have a constant access to the bladder. He also provides for antibacterial seals to prevent bacteria from entering the urinary tract.

Glassman has developed a catheter with grooves along the exterior wall through which a cleansing solution can irrigate the urethra. The solution is introduced into the catheter through an external tube which directs the solution through channels within the wall of the catheter and into the grooves through openings spaced along its length. The cleansing solution does not enter the bladder, nor does it cleanse the drainage lumen. (U.S. Pat. No. 4,579,554).

Sakamoto et al. in U.S. Pat. No. 4,642,104, teaches a process for affixing an antimicrobial substance to the exterior wall of a urinary catheter to effectively prevent urinary tract infection. The antimicrobial substance is effective over an extended period of time.

None of the above patents are for introduction of the irrigating solution into the bladder itself. Chen et al. in U.S. Pat. No. 4,904,245 has developed a valve assembly for urinary bladder irrigation. However, that system introduces the irrigating solution through the same channel used for drainage, thus pushing any material within the lumen of the catheter up into the bladder.

Morales et al. designed a catheter through which urine is drained from the bladder and which also delivers medication to the bladder through a separate central channel. This catheter is not indwelling and is removed after the medication has been dispensed. (U.S. Pat. No. 5,120,316)

Chaffin (U.S. Pat. No. 2,286,462) developed a surgical drainage and irrigation tube. The irrigating solution flows upwards on one arm of the tube, and down the other arm. Some of the solution can enter the surgical field, but it is the downward flow that creates mild suction to remove blood and other secretions from the field without creating negative pressures in the cavity or wound.

The instant invention proposes a catheter which can deliver an irrigating solution to the bladder, provide drainage of urine from the bladder and also maintain a mild suction to break up and remove clots and debris which may clog the drainage ports. The drainage lumen of the catheter is cleansed at the same time, thus lessening the chance of upward movement of bacterial therein.

BRIEF SUMMARY OF THE INVENTION

After bladder and prostate surgery the bladder must be irrigated regularly. Often blood clots form in the bladder which must be broken up and flushed out. This is a painful process adding to the usual discomfort of the surgery itself. A continuous irrigation of the bladder will alleviate the discomfort by preventing distention caused by forcing the solution up through the lumen of the catheter at periodic intervals. Pressurized liquid forced through the main lumen of the catheter would still be possible at such time as clots block the drainage ports and cannot be dislodged by the mild suction created by the reverse flow of the irrigating solution in the catheter of the present invention.

Additionally, the usual irrigation of the bladder using positive pressure often results in spasms of the bladder when the catheter is removed. The use of continuous but low level irrigation should eliminate this problem.

It is an object of the present invention to have a urinary catheter capable of delivering a sterile irrigating solution directly into the bladder through a lumen other than the one for drainage of urine from the bladder so as not to reintroduce harmful bacteria into the bladder during irrigation.

It is another object of the present invention to have the delivery channel for the irrigating solution small as compared to the drainage lumen such that the irrigating solution is delivered continuously but in small quantities.

It is a further object of the present invention to cause the irrigating solution to flow into the catheter under slight pressure and pass directly into a small central lumen, and to have a portion of said irrigating solution enter directly into the bladder.

A further object of the present invention is to have a large percentage of the irrigating solution be deflected downward by a cone shaped structure located within the distal tip of the catheter. This deflection and reverse flow creates a mild venturi suction which aides in drawing clots and debris from the bladder through the drainage ports. The suction thus resulting is mild enough for drainage purposes but does not create a negative pressure within the bladder.

Another object of the present invention is to have the irrigating solution cleanse the drainage lumen during its downward flow so as to flush out bacteria and other debris.

Another object of the present invention is to permit the use of a suction syringe should a large blockage occur which cannot be dislodged during the normal irrigation process, with the added advantage of having the drainage lumen in a cleansed condition at all times.

A second embodiment of the present invention contains small protuberances affixed to the central tube blow the level of the drainage ports, the object of which is to assist in breaking up any large clots or tissue clumps which are drawn through the drainage ports by the suction.

Other features and advantages of the invention will be seen from the following description and drawings.

BRIEF DESCRIPTION OF THE DRAWINGS

FIG. 1 is a perspective view of the urinary catheter of the present invention.

FIG. 2 is a longitudinal transverse section of the catheter shown in FIG. 1.

FIG. 3 is an enlarged cross section view taken along line 3—3 of FIG. 2.

DETAILED DESCRIPTION OF THE INVENTION

Figure 7:
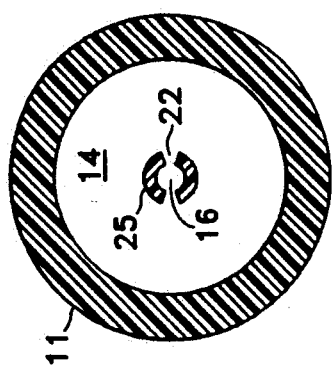
FIG. 7 is a cross sectional view taken along line 7—7 of FIG. 6.

The urinary catheter 10 of the present invention is an improvement over the well known Foley catheter. It is designed to be inserted through the urethral canal into the bladder. Once in place, an expandable balloon 15 surrounding a portion of the distal end of the catheter 10 is inflated and retains the catheter in position. A plurality of lumina provide separate drainage, irrigation and balloon inflation means.

As seen in FIG. 1, the catheter 10 has a rounded distal tip 19 at its distal end and terminates in three separate tubes 11, 12 and 13 at the proximal end. Catheter 10 has a main or drainage lumen 14 within tube 11 which extends substantially its entire length. A second smaller lumen 16 within tube 13 is centrally disposed and also extends substantially the entire length of the catheter 10. It is through the central lumen 16 that the irrigating solution is delivered. A third channel 17, located within the wall of tube 11 and communicating with exterior tube 12 permits inflation and deflation of the retention balloon 15. Channel 17 terminates in opening 18 into the inflation balloon 15. (FIGS. 2 and 3) Tubes 11, 12 and 13 at the proximal end are fitted with leakproof sealable connectors known in the art and not illustrated or further described herein.

Once inserted in the bladder, the balloon 15 is inflated and the connector sealed. The catheter is retained in place within the bladder until the balloon 15 is deflated for removal.

Figure 6:
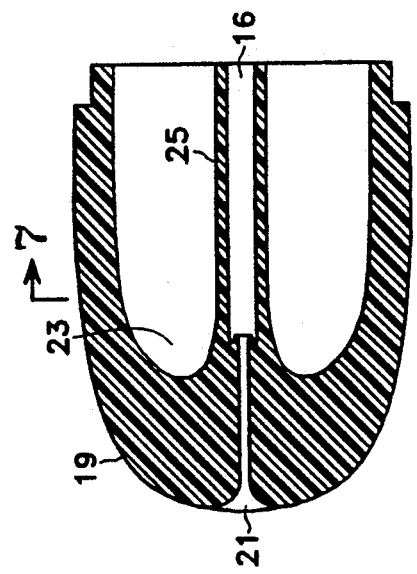
FIG. 6 is an enlarged longitudinal transverse section view taken along line 6—6 of FIG. 4.
Figure 4:
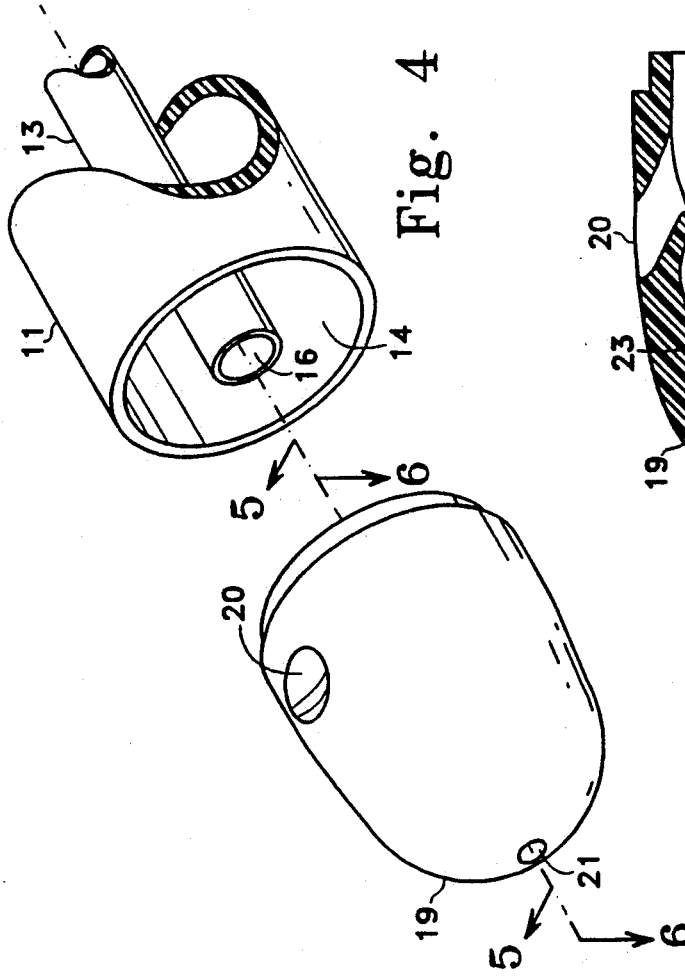
FIG. 4 is an exploded view of the distal end of the catheter of FIG. 1.
Figure 5:
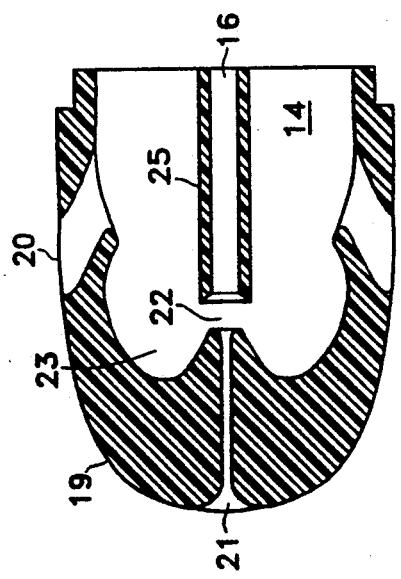
FIG. 5 is an enlarged longitudinal transverse section view taken along line 5—5 of FIG. 4.

The internal structure of the catheter 10 can be seen in FIG. 2. The outer tube 11 is fused to the distal tip 19 which is molded separately. The interior roof 23 of the distal tip 19 is cone-shaped and there is a feed port 21 at the apex. At least two drainage ports 20 are located at the sides of distal tip 19. There are two opposing members 25 extending from the interior roof 23 (FIG. 6). Distal tip 19 is uniquely constructed to be fused circumferentially to the distal end of outer tube 11, and is fused through members 25, to the distal end of interior tube 13, leaving openings 22 disposed therebetween (FIGS. 4, 5 and 7).

The irrigating solution is introduced from a container located at least four feet above the patient's bed and connected at the proximal end of the catheter to tube 13. This height creates a positive pressure forcing the solution through the central lumen 16. A small portion of the solution enters the bladder by way of feed port 21 in the center of the distal tip 19. The remainder of the solution passes through openings 22, strikes the cone shaped interior roof 23 of distal tip 19 and is deflected downward past drainage ports 20. As the irrigating solution flows downward past the drainage ports 20, the mild venturi suction created therefrom aids in drawing urine, blood clots and tissue debris from the bladder through the drainage ports 20 and into the drainage lumen 14 of the catheter 10. The flow pattern of the irrigating solution can be seen in FIG. 8. The continuous downward flow of solution also serves to cleanse the drainage lumen 14 and prevents the upward movement and build-up of bacteria which is characteristic of most indwelling urinary catheters. The solution and debris from the bladder move downward by gravity and are collected in the drainage bag located below the level of the patient's bed.

Figure 8:
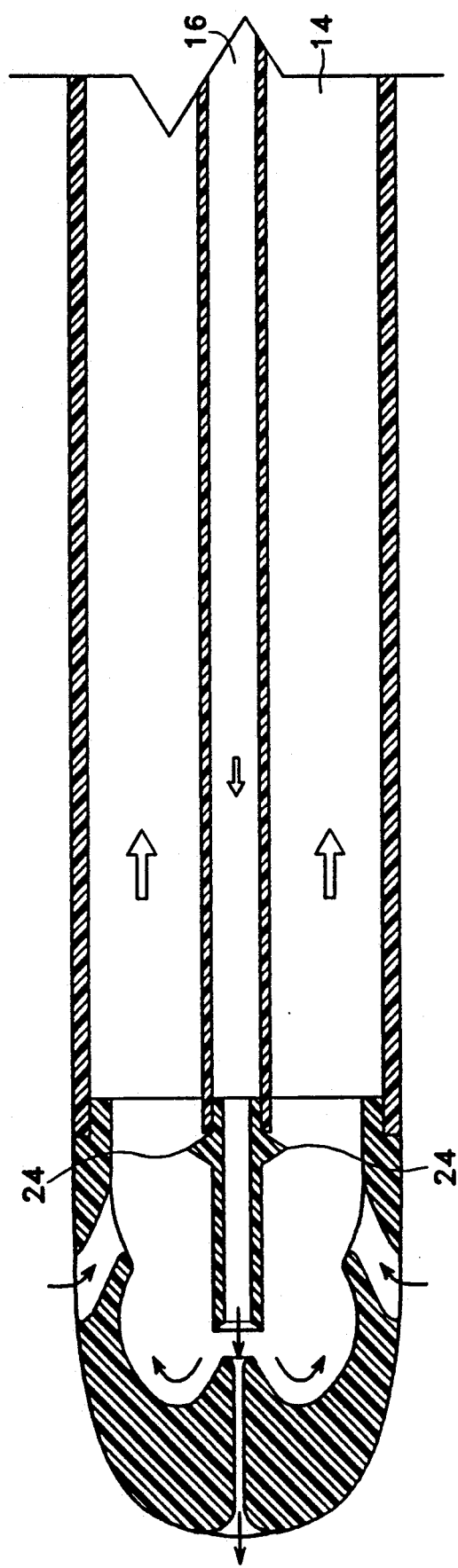
FIG. 8 is an enlarged longitudinal transverse section of the distal end of a second embodiment of the present invention and showing the flow direction of the irrigating solution.

A second embodiment of the present invention has one additional feature. There are two clot breaking protuberances 24, as seen in FIG. 8, located in distal tip 19. The protuberances 24 are integral with members 25, are located across from and slightly below the drainage ports 20 and function to break up clots and clumps of tissue debris as they are drawn from the bladder into the main lumen 14.

In the event that the mild suction is not sufficient to dislodge clots blocking the drainage ports 20, a suction syringe can be used in the usual manner by connection to main tube 11, with the added advantage of having the drainage lumen 14 in a cleansed condition so as to prevent bacteria from being forced backward into the bladder.

The catheter of the present invention, including the distal tip can be constructed of a variety of biologically inert, soft and flexible polymeric materials known in the art. The exterior roof of the distal tip 19 is rounded and non-rigid to facilitate insertion and minimize damage to delicate tissue.

The dimensions of the catheter can vary both as to length and diameter as needed. The external leakproof sealable connectors at the proximal ends of tubes 11, 12 and 13 can be of varied forms known in the art.

While two embodiments of the present invention have been illustrated and described in detail, it is to be understood that this invention is not limited thereto and may be otherwise practiced within the scope of the following claims.

We claim:

1. A catheter adaptable for insertion into a body cavity and capable of delivering an irrigating solution thereto and of providing a mild suction to assist in the removal of waste materials such as blood clots, bacteria, fluids and tissue debris therefrom, said catheter comprising:
   a substantially flexible tube means having a proximal end and a distal end;
   first and second lumina extending substantially the length of said tube, said first lumen for drainage of the waste materials from the body cavity and said second lumen for delivery of the irrigating solution to the body cavity;
   tip means integral with the distal end of said tube;
   delivery means defining an aperture centrally disposed in said tip, said aperture being fluidly connected to said second lumen for administering the irrigating solution into the body cavity;
   drainage means defining at least two drainage ports laterally disposed in said tip, said drainage ports being fluidly connected to said first lumen for removal of the waste materials from the body cavity;
   oriface means within said tip defining a passage for entry of said irrigating solution from said second lumen into said first lumen such that the irrigating solution cleanses the length of the first lumen;
   deflection means within said tip to deflect said irrigating solution downward and past said drainage ports such that the downward flow creates the suction to assist removal of the waste materials from the body cavity; and
   separate external means at the proximal end of the tube for communication with said first and second lumina.

2. A catheter as defined in claim 1 further comprising a circumferential inflatable membrane disposed near the distal end of said catheter, an inflation duct in communication with said membrane, and means for inflating said membrane, for retention of the catheter in the body cavity.

3. A catheter as in claim 1 constructed of a flexible, biologically inert polymeric material.

4. A soft tip suitable for being integrally and permanently mounted at the distal end of a catheter having at least two lumina, said tip comprising:
   an exterior roof and an interior ceiling, said roof being rounded for ease of insertion into a body cavity;
   delivery means defining an aperture centrally disposed in said tip, said aperture being fluidly connected with the second lumen for delivery of solution into the body cavity;
   drainage means defining at least two drainage ports laterally disposed in said tip, said drainage ports being fluidly connected with the first lumen for removal of waste materials from the body cavity;
   oriface means within said tip defining a passage for entry of said solution from said second lumen into said first lumen; and
   deflection means within said tip to deflect said solution downward and past said drainage ports such that the downward flow creates suction to assist removal of the waste materials from the body cavity, said deflection means being a concavity in the ceiling.

5. A tip as in claim 4 constructed of a flexible, biologically inert polymeric material.

6. A catheter adaptable for insertion into a body cavity and capable of delivering an irrigating solution thereto and of providing a mild suction to assist in the removal of waste materials such as blood clots, bacteria, fluids and tissue debris therefrom, said catheter comprising:
   a substantially flexible tube means having a proximal end and a distal end; first and second lumina extending substantially the length of said tube, said first lumen for drainage of the waste materials from the body cavity and said second lumen for delivery of the irrigating solution to the body cavity;
   tip means integral with the distal end of said tube;
   delivery means defining an aperture centrally disposed in said tip, said aperture being fluidly connected to said second lumen for administering the irrigating solution into the body cavity;
   drainage means defining at least two drainage ports laterally disposed in said tip, said drainage ports being fluidly connected to said first lumen for removal of the waste materials from the body cavity;
   at least two clot breaking members disposed opposite and below said drainage ports;
   oriface means within said tip defining a passage for entry of said irrigating solution from said second lumen into said first lumen such that the irrigating solution cleanses the length of the first lumen;
   deflection means within said tip to deflect said irrigating solution downward and past said drainage ports such that the downward flow creates the suction to assist removal of the waste materials from the body cavity; and
   separate external means at the proximal end of the tube for communication with said first and second lumina.

7. A catheter as defined in claim 6 further comprising a circumferential inflatable membrane disposed near the distal end of said catheter, an inflation duct in communication with said membrane, and means for inflating said membrane for retention of the catheter in the body cavity.

8. A catheter as defined in claim 6 constructed of a flexible, biologically inert polymeric material.

9. A soft tip suitable for being integrally and permanently mounted at the distal end of a catheter having at least two lumina, said tip comprising:
   an exterior roof and an interior ceiling, said roof being rounded for ease of insertion into a body cavity;
   delivery means defining an aperture centrally disposed in said tip, said aperture being fluidly connected with the second lumen for delivery of solution into the body cavity;
   drainage means defining at least two drainage ports laterally disposed in said tip, said drainage ports being fluidly connected with the first lumen for removal of waste materials from the body cavity;

at least two clot breaking members disposed opposite and below said drainage ports;

oriface means within said tip defining a passage for entry of said solution from said second lumen into said first lumen; and deflection means within said tip to deflect said solution downward and past said drainage ports such that the downward flow creates suction to assist removal of the waste materials from the body cavity, said deflection means being a concavity in the ceiling.

10. A tip as in claim 9 constructed of a flexible, biologically inert polymeric material.

* * * * *